United States Patent [19]

Kralovic et al.

[11] Patent Number: 4,892,706
[45] Date of Patent: * Jan. 9, 1990

[54] AUTOMATED LIQUID STERILIZATION SYSTEM

[75] Inventors: Raymond C. Kralovic, Springfield, Pa.; Edward T. Schneider, Mentor, Ohio

[73] Assignee: Steris Corporation, Painesville, Ohio

[*] Notice: The portion of the term of this patent subsequent to Mar. 15, 2005 has been disclaimed.

[21] Appl. No.: 140,388

[22] Filed: Jan. 4, 1988

Related U.S. Application Data

[63] Continuation-in-part of Ser. No. 826,730, Feb. 6, 1986, Pat. No. 4,731,222.

[51] Int. Cl.$^4$ .......................... A61L 2/18; A61L 2/24; C23F 13/00
[52] U.S. Cl. ..................... 422/28; 204/147; 422/37; 422/292; 422/307
[58] Field of Search ................ 422/28, 292, 307, 37; 204/147

[56] References Cited

U.S. PATENT DOCUMENTS 3,893,832  8/1975  Perry et al. .......................... 55/268
4,552,728  11/1985  Taylor .................................. 422/300
4,731,222  3/1988  Kralovic et al. ................ 422/28 X

FOREIGN PATENT DOCUMENTS 2749448  5/1979  Fed. Rep. of Germany .
 008419  4/1984  Fed. Rep. of Germany .
3339930  5/1985  Fed. Rep. of Germany .

OTHER PUBLICATIONS

Block, *Disinfection, Sterilization & Preservation*, 3rd Ed. Lea & Febiger, Philadelphia, 1983, pp. 245–246.

Primary Examiner—Barry S. Richman
Assistant Examiner—Jill Johnston
Attorney, Agent, or Firm—Fay, Sharpe, Beall, Fagan, Minnich & McKee

[57] ABSTRACT

Each of a plurality of modules (A) have fitings (14) with automatically closed check valves (16) therein such that the interior of the module is sealed. The module is selectively interconnected with a sterilizer apparatus (B). Interconnecting tubing (60) selectively supplied liquid from a reservoir (30) to the module. A sterilant injection chamber (56) receives and punctures a sterilant ampule such that incoming water mixes with the sterilant concentrate forming a sterilant solution which is carried to the reservoir. A reservoir outlet valve (70) selectively permits the sterilant solution to pass from the reservoir through the interconnecting tubing into the module until the module and interconnecting tubing are completely filled. Thereafter, the reservoir outlet valve closes holding the sterilant in the interconnecting tubing as well as the module for sufficient duration to sterilize both. Concurrently, additional tap water is heated in the reservoir until it is sterile. Alternate means of sterilizing the rinse fluid may also be employed. Thereafter, the reservoir outlet valve is opened again and the sterilant solution is drained and rinsed from the module with the sterile water. An air pump (86), a heater (84), and a submicron sterilization filter (82) supply heated, sterile drying air through the reservoir, connecting tubing, and module to dry the sterilized device.

17 Claims, 2 Drawing Sheets

AUTOMATED LIQUID STERILIZATION SYSTEM

BACKGROUND OF THE INVENTION

This application is a continuation-in-part of U.S. patent application Ser. No. 826,730, filed on Feb. 6, 1986, now U.S. Pat. No. 4,731,222, issued Mar. 15, 1988.

The present invention pertains to the sterilization art. The present invention finds particular application in conjunction with the sterilization of medical devices and will described with particular reference thereto. It is to be appreciated, however, that the invention may also find application in the sterilization, disinfecting, and liquid immersion treatment of other devices.

Sterilization is defined as the absence of all life forms including bacterial endospores which are the living organisms most resistant to known sterilants. Disinfection, by distinction, only connotes the absence of pathogenic life forms.

A sterilizer or sterilizing apparatus must demonstrate sporicidal activity which meets the standards specified in the United States Pharmacopeoia (20th revision; U.S. Pharmacopeoia Convention Inc.; Rockville, MD) or the standards of the Association of Official Analytical Chemists (Official Methods of Analysis; 13th edition; Washington, D.C.). It is to be appreciated that establishing the absence of all life forms in sterilization is more readily documented and controlled than the elimination of pathogenic but not all life forms in disinfection.

Some high level disinfectants, such as glutaraldehyde and stabilized hydrogen peroxide, are also sporicidal. However, the six to eight hours required for 2% glutaraldehyde to achieve sterilization renders it impractical as a sterilant. Disinfection is, of course, achieved in a considerably shorter exposure time. Commercially, substantially all high level disinfectants are utilized in liquid form. Liquid sterilization and disinfecting processes immerse the item to be sterilized in a bath or vat of the sterilizing or disinfecting liquid.

Because bacterial spores are the life form which is most resistant to sterilants, they are commonly used as reproducible, stable indicators of the effectiveness of a sterilization process. In the medical industry, a sterility assurance level (SAL) of less than or equal to one chance in one million of having a contaminated item is generally regarded as the minimum acceptable level for medical devices which are designed to be used in sterile tissues of the human body. In practice, this level of assurance is obtained by establishing the exposure time required to sterilize a given quantity of bacterial endospores known to be resistant to the sterilant. *Bacillus stearothermophilus* is a suitable indicator for steam or moist heat sterilization and spores of *Bacillus subtilus* are suitable indicators for dry heat or ethylene oxide sterilization. The rate of destruction of the spores at the sterilization conditions is expressed as the time required to reduce the viable spore population by 90% or 1 log. This destruction rate is commonly referenced as the D value. From the D value, which is a rate function, the time required for a given sterility assurance level can be calculated. For example, spores of *Bacillus stearothermophilus* typically have a D value in saturated steam of 250° F. and 15 psig of two minutes. Thus, an item with 100 spores ($10^2$) will have the spore count reduced to one spore ($10^0$) in four minutes, i.e. a 2 log reduction. Because sterility requires an assurance level of one in a million ($10^{-6}$), an additional exposure time of 12 minutes ($6 \times 2$ minutes) or a total exposure time of 16 minutes is required for complete sterilization.

Pathogenic microorganisms, which are mostly vegetative forms of bacteria, do not have the stability to enable a D value or the equivalent to be derived after storage. There is no accompanying biological indicator applicable to pathogenic organisms which functions as a reliable, reproducible, and stable indicator of the effectiveness of the disinfection process. Accordingly, assuring that disinfection has occurred is more difficult and unreliable than assuring sterilization.

This inability to assure the effectiveness of disinfectants with biological indicators is compounded by the lack of easily measured physical parameters which demonstrate in minimal necessary conditions for disinfection. For liquid disinfectants, the active agent must be measured in individual discrete samples by a wet chemical method. Such methods are not easily automated nor do they provide continuous real time monitoring. Accordingly, liquid disinfectants are generally considered unsuitable for use by unskilled personnel.

Another problem compounding use of liquid disinfectants is that the active agent is commonly toxic to human tissue and must be removed by rinsing with water. Frequently, tap water is used as the rinse. However, the same microorganisms that are killed by the disinfectant are found in tap water and can be redeposited therefrom. Thus, the tap water rinse may defeat the disinfection process. Because sterile rinse water or saline are relatively expensive, there is a tendency for medical facilities to use a minimal amount of sterile rinse which frequently leaves a disinfectant chemical residue.

Yet another drawback to liquid disinfection processes is that the disinfected state cannot be maintained. No effective packaging or containment systems are available which can guarantee the preservation of the disinfected state of an item until use. Thus, with disinfection, a patient is apt to be exposed to both chemical residue and biological risks.

Despite the shortcomings of liquid disinfectants, vast quantities are used for disinfecting medical devices. Many of these medical devices are made of plastic or have complex lens systems, e.g. rigid or flexible endoscopes. The plastic elements and lens system may be destroyed or have their useful lives severely curtailed by thermal sterilization systems such as steam. Conventional ethylene oxide sterilization (which is thermally less severe than steam) requires a relatively long exposure time, on the order of three and a half hours. Ethylene oxide, which is relatively expensive compared to liquid sterilants, requires an even longer aeration time, on the order of 8-12 hours. The pressure excursions of the ethylene oxide sterilization equipment may damage lens instruments. Because ethylene oxide is a toxic, volatile gas, operator safety is a serious concern.

Accordingly, liquid sterilants rather than gaseous sterilants are commonly used for disinfection of heat sensitive and expensive medical devices in medical facilities. Liquid sterilants are rapid when used to achieve disinfection, cost effective, and do minimal damage to medical devices. However, the prior art liquid sterilant/disinfection methods and apparatus are lacking in assurance and reproducibility of disinfection, removal of chemical residues, safety, cost, and the ability to preserve the disinfected or sterile state until reuse. In addition, normal methods for the use of liquid sterilants can produce only a disinfected state because methods to produce and preserve the sterile state have not been available.

In accordance with the present invention, a new and improved liquid sterilization method and apparatus are provided which overcomes the above referenced problems and others.

Summary of the Invention

In accordance with one aspect of the present invention, a method of sterilization is provided. Both a module containing at least one item to be sterilized and tubing which interconnects the module with a sterile rinse solution reservoir are filled with a sterilant solution. The sterilant solution is held in both the module and the interconnecting tubing for a preselected duration which is sufficiently long to assure sterilization of the module, the item, and the interconnecting tubing. The sterilant solution is rinsed from the interconnecting tubing, the module and the item with sterile rinse solution from the rinse solution reservoir.

In accordance with more limited aspects of the invention, tap water is heat sterilized in the rinse solution reservoir to create the sterile rinse solution. A sterile, drying gas is passed through the interconnecting tubing and the module to dry the sterilized item. An electrical current is passed between the item and the sterilant solution to inhibit galvanic corrosion during the sterilization. After the module and item are dried, the module with the item still encased therein are stored and inventoried as a unit until needed for use.

In accordance with another aspect of the present invention, a method of sterilizing is provided. An item to be sterilized is enclosed in a module which is closed to the ambient atmosphere. A preselected dose of sterilant concentrate is discharged into a dilution fluid to form a sterilant solution. The sterilant solution fills and is held in the module until the item is sterilized. Thereafter, the sterilant solution is discarded such that fresh sterilant solution is used for each sterilization. A sterile rinse fluid is passed through the module to rinse the sterilant solution from the item. The item is stored in the module to retain the item sterile until one is ready to use it.

The present invention also contemplates a method of disinfection which inhibits galvanic corrosion. An item immersed in a disinfectant solution is cathodically protected either with a sacrificial anode or by applying an electrical potential between the item and an electrode in the solution. Alternatively, chemical corrosion inhibitors may be employed to protect metal surfaces from galvanic or other corrosion forces caused by their interaction with a liquid chemical sterilizer.

In accordance with another aspect of the present invention, a sterilization apparatus is provided. A module contains at least one item to be sterilized. A reservoir for holding a sterile rinse solution is connected with the module by interconnecting tubing such that the sterile rinse solution can selectively pass from the reservoir to the module. A means is provided for selectively filling both the interconnecting tubing and the module with a sterilant solution. Another means is provided for selectively holding the sterilant solution in the interconnecting tubing and module for a preselected duration.

In accordance with more limited aspects of the invention, the reservoir includes heating means for heat sterilizing received tap water or other rinse solutions. A sterile air supplying means selectively supplies sterile air through the reservoir, interconnecting tubing, and the module for drying the sterilized item. Electrodes may be provided in the module for providing cathodic protection during either sterilization or disinfection processes to inhibit galvanic corrosion. Alternatively, chemical corrosion inhibitors may be employed by dissolution simultaneously with or before dissolution of the sterilant solution and exposure of devices to be sterilized to the liquid chemical sterilant.

One advantage of the present invention is that it produces a high sterility assurance level (SAL).

Another advantage of the present invention is that it avoids thermal degradation to the sterilized devices.

Further advantages reside in increased operator safety, greater cost efficiency, and longer shelf life of sterilized devices.

Still further advantages will become apparent to those of ordinary skill in the art upon reading and understanding the following detailed description of the preferred embodiment.

BRIEF DESCRIPTION OF THE DRAWINGS

The invention may take form in various steps and arrangements of steps and in various parts and arrangements of parts. The FIGURES are only for purposes of illustrating a preferred embodiment and are not to be construed as limiting the invention.

DETAILED DESCRIPTION OF THE PREFERRED EMBODIMENT

Figure 1:
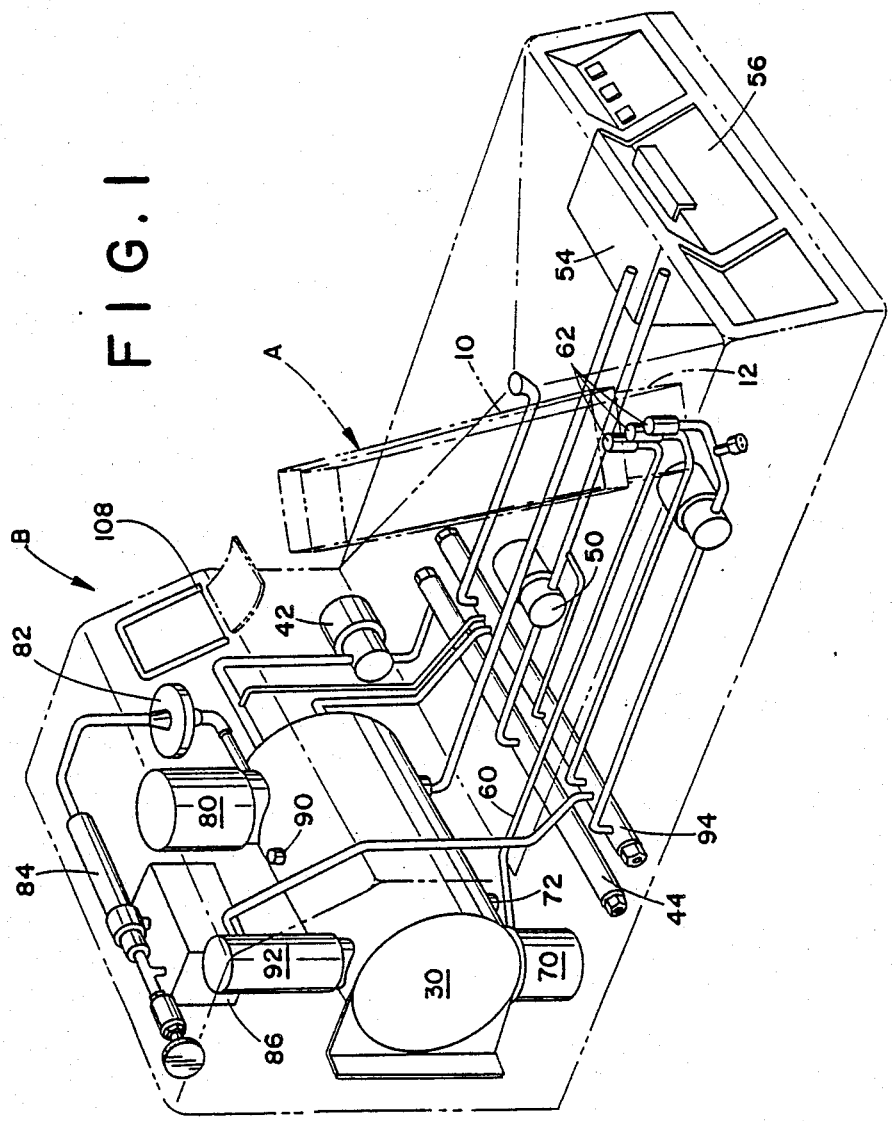
FIG. 1 is a perspective view in partial section of a sterilizing apparatus in accordance with the present invention with the housing and a module illustrated in phantom; and, FIG. 2 is a diagrammatic illustration of the sterilizing apparatus and module of FIG. 1.

With reference to FIG. 1, a module A for containing a medical device or other item to be sterilized is selectively interconnectable with a sterilizer apparatus B. Although the illustrated module is adapted to receive an endoscope, other shaped modules will be configured in accordance with the medical devices to be sterilized. During the sterilization process, the sterilization unit B serially supplies a sterilant solution, a sterile rinse solution, and a sterile drying gas to the module. The sterilant is held in the module and the plumbing of the unit through which the sterile rinse flows to the module for a sufficient duration to assure sterilization. During the hold or sterilization period, the unit heat sterilizes tap water or another suitable rinse solution. Optionally, other rinse water sterilization techniques may be used, such as radiation or further sterilization techniques. If desired, wetting, lubricant, anticorrosion agents and the like may be mixed with the rinse water. After the sterilization process, the sealed module, which is protected from microbiological contamination from the atmosphere, and the sterilized item are stored as a unit until the module is opened and the device is removed for use. This enables an inventory of sterilized items to be maintained. Because the items need not be sterilized immediately prior to use, the capacity of the sterilizer apparatus may be based on average sterile item useage of the medical facility rather than peak usage.

Figure 2:
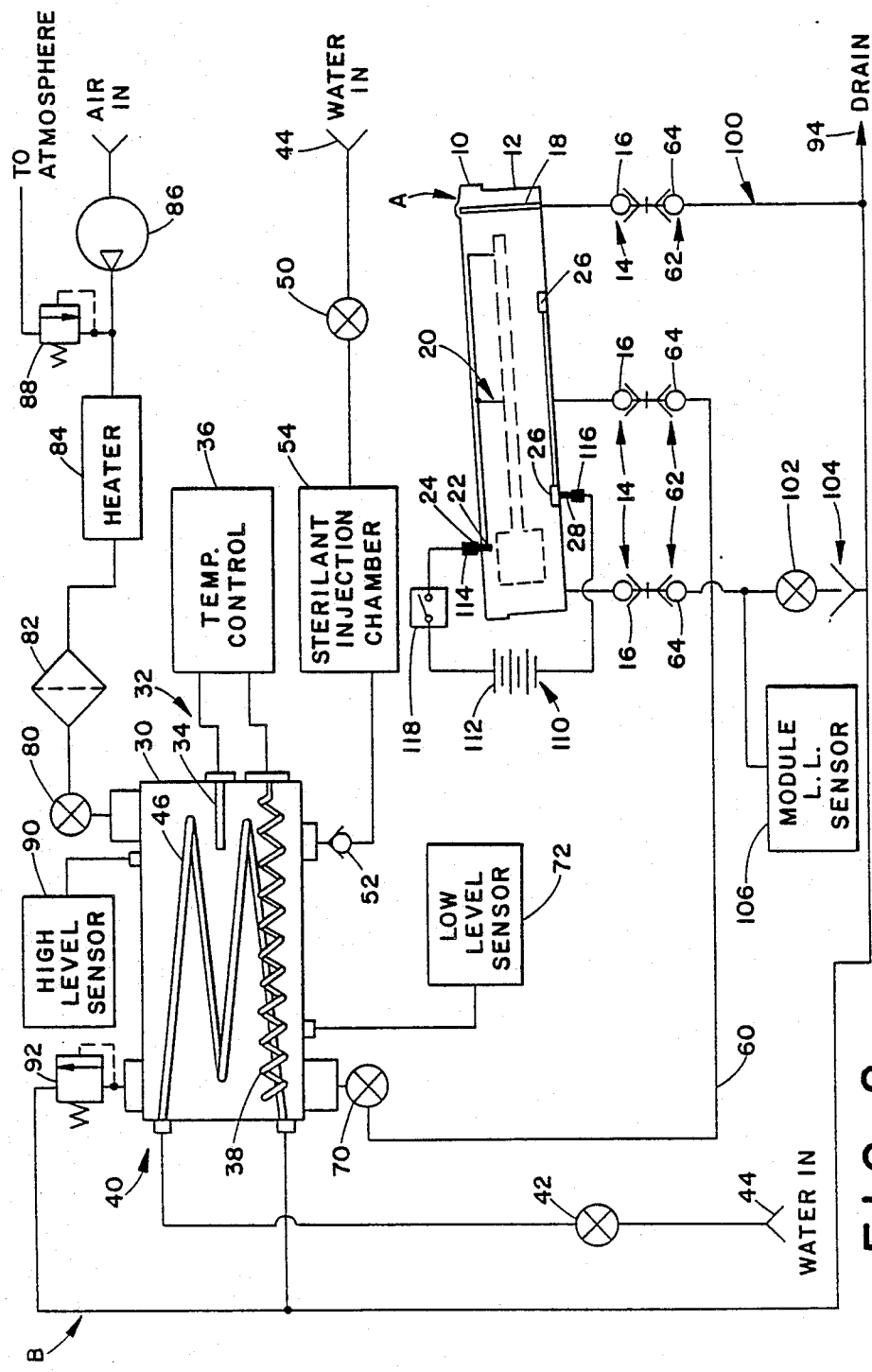

With particular reference to FIG. 2 and continuing reference to FIG. 1, the module A, which is protected from microbiological contamination from the atmosphere, is a sealed enclosure. A lid or cover 10 is opened to gain access to the interior of a body portion 12. Interconnection means or fittings 14 enable the module to be selectively connected in a fluid exchanging relationship to the sterilizer unit B. Fluid connections 16 are mounted in the interconnecting means to permit sterilant solution, rinse solution, and drying gas to pass into and out of the module only while it is interconnected with the sterilizer B. A fluid level control means such as a standpipe 18, or a liquid level sensor, assures that fluids completely fill the module and that ambient air is expelled. The module is mounted at an angle and the standpipe extends to the upper most point in the module to prevent air pockets. Concurrently with removal from the sterilizer, the check valves close to prevent, or a tortuous path prevents, ambient air contamination from entering the interior of the module. This enables the module and the sterilized item or items contained therein to be removed from the sterilizer as a unit and stored in inventory. Additional modules containing other items to be sterilized may be interconnected serially with the sterilizer B. After each item is sterilized, the item and its encasing module are also inventoried. In this manner, the self-sealing module enables an inventory of sterile devices to be maintained.

The module further includes a galvanic corrosion inhibiting means 20. In the preferred embodiment, an electrical connection means 22 electrically connects metal portions of the item to be sterilized with an exterior electrical connector 24. One or more interior electrodes 26 are connected with an exterior electrical connector 28. Under a suitable electrical bias applied by the sterilizer unit B, any galvanic current through the sterilant solution is neutralized. Optionally, other forms of cathodic protection, such as a sacrificial anode, may be provided. Alternatively, a chemical corrosion inhibitor may be provided.

The interior electrodes 26 may be constructed of an electrically conductive material with lower electrical potential than the item. For stainless steel and brass items, satisfactory anode materials include zinc, magnesium, aluminum, or the like.

A reservoir 30 is mounted in the sterilizer unit B such that the lowest surface of the reservoir is higher than the upper most surface of the module A. This enables fluid to flow under gravity from the reservoir and completely fill the module. Optionally, the reservoir may be mounted lower than the module and a pump provided. The reservoir includes an electrical heating means 32 for selectively heating liquids in the reservoir. A temperature sensor 34 monitors the temperature of the fluids in the reservoir. A temperature control means 36 selectively controls the electrical power through a resistive heating element 38 to maintain preselected liquid temperatures within the reservoir.

In the preferred embodiment, the temperature control means selectively heats a sterilant solution to 60° C. (140° F.) and boils water to 132° C. (270° F.). A cooling means 40 selectively reduces the temperature of the liquids in the reservoir. Specifically, a cooling water valve 42 selectively controls the flow of tap water from a water supply manifold or means 44 through a cooling coil 46. In a normal installation, the water manifold is connected with a sink or other water tap of the medical facility. In the preferred embodiment, tap water is sterilized by boiling at at least 132° C. and cooled below 60° C. before rinsing to avoid thermal degradation of the sterilized items. Alternatively, filter sterilization may be employed to provide a sterile water source.

The sterilant solution is formed by mixing a sterilant concentrate with tap water. A sterilant dilution or inlet water control valve 50 and a check valve 52 connect the water supply 44 with the reservoir 30. A sterilant injection chamber 54 is interconnected between the sterilant dilution water valve 50 and the check valve 52 for selectively injecting a sterilant concentrate into received tap water. Alternatively, a sterilant mixing chamber may be located in the sterilizing chamber itself. Further to the preferred embodiment, the sterilant injection chamber 54 receives a cartridge or ampule containing one or more components of a sterilant concentrate. Upon closing a cover 56 to the chamber, the sterilant cartridge is punctured such that the water may flow through the sterilant cartridge and wash the sterilant concentrate therefrom. The sterilant concentrate may be either a liquid, a solid, or combination thereof. In the preferred embodiment, the sterilant concentrate cartridge includes more than one compartment for containing peracetic acid segretated from a pH buffer and corrosion inhibiting chemicals or hypocholrite segregated from a pH buffer, a detergent and corrosion inhibiting chemicals.

Interconnecting tubing 60 interconnects the reservoir 30 and module receiving fluid connecting means 62. In the preferred embodiment, the module receiving connecting means include check valves 64 which close in the absence of a module to protect the interconnecting tubing from ambient contamination.

A tubing and module filling means or reservoir outlet valve 70, when open, selectively releases sterilant solution and rinse solution from the reservoir 30 to flow into and fill the interconnecting tubing 60 and the module A. When closed, the reservoir outlet valve 70 holds sterilant solution and other fluids in the interconnecting tubing 60 and the module A. The standpipe 18, or a suitable fluid level control means, prevents air pockets and assures that all surfaces of the interconnecting tubing, module, and item to be sterilized are held in contact with the sterilant solution for a preselected duration.

A low level sensor 72 senses when the liquid level in the reservoir reaches substantially to the bottom of the reservoir. When the liquid level reaches the bottom of the reservoir and before the liquid level clears the reservoir outlet valve 70, the low level sensor 72 closes the reservoir outlet valve 70 to trap and hold sterilant solution in the interconnecting tubing and module.

When the module A is mounted above the reservoir 30, a suitable conventional pump (not illustrated) is provided in the interconnecting tubing 60. The low level sensor 70 terminates operation of the pump sufficiently concurrently with the closing of the outlet valve 70 so that the interconnecting tubing and the pump chambers are completely filled with sterilant solution.

An air inlet valve 80 selectively interconnects the interior of the reservoir 30 with a source of sterile air or other drying gas. An air sterilizing means 82, such as a sterilizing filter which removes particulates which are as large or larger than bacteria, sterilizes received ambient air. Optionally, other sterilizing means may be utilized such as temperature, ozone, radiation, and the like. A heater 84 selectively heats the air to increase its drying power. An air pump 86 selectively supplies air under sufficient pressure to circulate the air or drying gas through the reservoir 30, the interconnecting tubing 60, and the module A. A pressure relief valve 88 selectively vents air from the reservoir as the reservoir is filled.

A high fluid level sensor 90 senses when the fluid completely fills in the reservoir 30 and the fluid level reaches the top of the reservoir. The high fluid level sensor 90 closes the water inlet control valve 50 when the liquid completely displaces all air from the reservoir and plumbing in fluid connection therewith. In this manner, the air inlet valve 80 is sterilized by steam as the rinse solution is heat sterilized. A pressure relief valve 92 interconnects the reservoir B with a drain 94 for permitting steam, excess water, or sterilant solution to be drained from the system. In a normal installation, the drain 94 is interconnected with the drain of a sink or other conventional plumbing.

When filling the module A and interconnecting tubing 60 with sterilant solution, a level control drain line 100 channels overflow sterilant solution from the standpipe 18 to the drain 94. At the end of the duration that sterilant solution is held in the interconnecting tubing and module, a drain valve 102 releases fluid from the module. The drain valve 102 selectively drains the sterilant and rinse solutions from the module through a siphon break 104 to the drain 94. At the end of the rinse cycle, a module empty sensor 106 senses that the module has been completely drained of liquid. After the module has been completely drained, the module low level sensor enables the air pump 86 and other portions of the drying assembly.

A printer 108 provides a printout of information concerning the sterilization process. In the preferred embodiment, the printer prints on a paper tape the date and time at which the sterilization was undertaken, the temperature of the sterilant solution as read by the temperature sensor 34 upon being introduced into the module, the duration which the sterilant was held in the module, the temperature to which the tap water was boiled and the duration of the boiling, and other system parameters. The paper tape or other appropriate print out is retained with the module and the sterlized item to provide a permanent record of the parameters of the sterilization process.

A galvanic corrosion inhibiting means 110 includes a source 112 of a D.C. electric potential. A first electrical contact 114 interconnects the electrical potential with the first module exterior electric connector 24 and the item to be sterilized. A second electric contact 116 interconnects the electric potential with the second module exterior electric connector 28 and the interior electrodes 26. A switch 118 connects the source of electric potential with the module while sterilant solution is held therein and disconnects the potential source at other times. Altenatively, a sacrificial metal or chemical corrosion inhibitors can be employed. When the electrodes 26 are constructed of a sacrificial metal, the source of electrical potential may be omitted.

In operation, a contaminated device is closed in the module A and the module is plugged into the sterilizer unit B. A sterilant cartridge is placed in the sterilant injection chamber 54 and the chamber is closed. The sterilizer is now ready for automatic operation.

The sterilizer B first opens the water inlet control valve 50 which dilutes and, if applicable, dissolves components of the sterilant concentrate forming a sterilant solution. The sterilant solution passes into the reservoir 30 until the high level sensor 90 senses that the reservoir is completely filled.

The high level sensor 90 causes the inlet water control valve 50 to close and the temperature control means 36 to heat the sterilant solution to 60° C. for two to three minutes. The reservoir outlet valve 70 opens allowing the warm sterilant solution to flow through and fill the interconnecting tubing 60 into the module A. When the module is completely filled, excess sterilant solution flows through the standpipe 18 to the drain 94.

When the reservoir low level sensor 72 senses that the level of sterilant in the tank is almost to the bottom, the reservoir outlet valve 70 is caused to close. Closing the reservoir outlet valve 70 traps and holds the sterilant in the interconnecting tubing 60 and the module A. The sterilant solution is held in the interconnecting tubing and module for a suffient duration to sterilize the tubing, the module, and the item held in the module, in the preferred embodiment a minimum of about 10 minutes. The whole duration is calculated such that the chances of a surviving life form is no greater than one in one million, that is, a sterility assurance level of $10^{-6}$. While the sterilant solution is in the module, switch 118 is closed causing a current flow between the module electrode 26 and the item being sterilized to inhibit galvanic corrosion.

While the sterilant is being held in the module A and interconnecting tubing 60, the water inlet valve 50 is again opened to fill the reservoir 30 with additional tap water. The incoming tap water flows through the sterilant concentrate cartridge which has been fully emptied. Optionally, the same cartridge or another cartridge may include another chamber holding a rinse water treatment and the sterilizer unit B may channel the incoming tap water therethrough. The treatment may include a salt, a pH buffer, a filter, or the like. When the high liquid level sensor 90 senses that the tap water has filled the reservoir completely, the water inlet control valve 50 is closed and the temperature control means 36 causes the water to be heated to a sterilization temperature, e.g. 132° C. for at least five minutes. After the rinse water has been heat sterilized, the cooling water valve 42 is opened to reduce the temperature of the rinse water in the reservoir 30 below 60° C. to avoid heat degradation of the sterilized device. It should be understood that when other means of sterilization are employed, e.g. filter sterilization, the reservoir and holding tank may be eliminated and the sterile water generated on a demand basis.

After the sterilization period, drain valve 102 and the reservoir outlet valve 70 are opened allowing the sterilant solution to drain from the module and allowing the rinse solution to rinse the interconnecting tubing 60, the module A, and the sterilized item with sterile rinse solution.

When the module is empty, the module low level sensor 106 senses that the sterilant solution and the rinse solution have been drained from the module. The air pump 86 and air heater 84 are actuated to supply a flow of hot air. The air sterilizing filter 82 removes living organisms and other particles of comparable size such that only sterile, warm air passes through the reservoir 30, the connecting tubing 60, the module A, and out the siphon break 104. The warm air may be circulated through the module for a sufficient time to cause complete drying of the device. Alternately, the module may include a liquid impermeable submicron sterilization filter which allows water vapor to pass out of the module without allowing bacteria and other potential contaminants to enter. If the module has such a permeable filter port, the module may be removed from the sterilizer before complete drying.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A method of sterilizing medical instruments, the method comprising:
   disposing a medical instrument to be sterilized in a storage module;
   closing the module to penetration by microbial contamination;
   removably attaching the storage module with tubing which interconnects the attached module with a source of liquid rinse solution;
   completely filling the interconnecting tubing from the module to the rinse solution source and the module with a liquid sterilant which includes peracetic acid;
   retaining the liquid sterilant in the module and the interconnecting tubing for a pre-selected duration, which pre-selected duration is sufficiently long to sterilize the module, the medical instrument, and the interconnecting tubing;
   passing a sterilized liquid rinse solution from the rinse solution source only through the sterilized interconnecting tubing into the sterilized module to rinse the liquid sterilant from the interconnecting tubing, the module, and the medical instrument, whereby the liquid rinse solution passes only in contact with sterilized surfaces to prevent contamination of the liquid rinse solution;
   detaching the module from the interconnecting tubing while maintaining the module closed to microbial contamination; and,
   storing the module and the medical instrument as a unit.

2. The sterilization method as set forth in claim 1 further including mixing a sterilant concentrate with tap water to form the liquid sterilant.

3. The sterilization method as set forth in claim 1 further including:
   during the liquid sterilant retaining step, passing an electrical current between the medical instrument to be sterilized and an electrode in an electrical conductive relationship with the liquid sterilant to inhibit galvanic corrosion.

4. The sterilization method as set forth in claim 1 wherein the liquid sterilant is a solution which includes said peracetic acid together with a buffer, and water.

5. The sterilization method as set forth in claim 1 further including, during the liquid sterilant retaining step, the step of employing corrosion inhibitors.

6. A method of sterilizing items comprising:
   (a) enclosing an item to be sterilized in an interior of a module which is closed to penetration of microbial contaminants from the ambient atmosphere;
   (b) removeably attaching the module with tubing that connects the module with a source of sterile rinse liquid;
   (c) causing a liquid sterilant which includes peracetic acid to flow into and remain in contact with the module interior and the tubing which connects the module with the source of sterile rinse liquid until the item and the module interior are sterilized;
   (d) draining the liquid sterilant from the module interior;
   (e) passing a sterile rinse liquid from the source thereof into the module interior to rinse the item;
   (f) detaching the module while maintaining the module closed to microbial contaminants;
   (g) storing the item in the module to retain the item in a sterile condition.

7. The method as set forth in claim 6 further including after step (e), passing a bacteria-free gas into the module interior.

8. The method as set forth in claim 6 wherein the liquid sterilant is a solution including said peracetic acid together with a buffer and water.

9. A method of sterilizing comprising:
   enclosing an item to be sterilized in a sterilizing chamber which is isolated from microbial contamination from the ambient atmosphere;
   providing interior surfaces which define a liquid rinse flow path between the chamber and a source of sterile rinse liquid;
   causing a liquid sterilant which includes peracetic acid to flow into the chamber and into all flow path interior surfaces which define the interconnecting flow path from the sterile liquid rinse source into the chamber and every interior surface in direct fluid communication therewith;
   retaining the liquid sterilant in the chamber and the interior surfaces until the interior surfaces, the item, and the chamber are sterilized, whereby sterilizing all surfaces between the rinse fluid source and the chamber assures that the liquid rinse fluid will not carry microbial contaminants from non-sterile surfaces into the chamber;
   draining the liquid sterilant from the chamber and the interconnecting flow path;
   passing the sterile liquid rinse fluid from the liquid rinse source only in contact with the sterilized flow path surfaces into the chamber to rinse the item;
   draining the liquid rinse fluid from the chamber and the interconnecting flow path.

10. The method as set forth in claim 9 further including during the draining step, passing bacteria-free air into the chamber to dry the item and the chamber interior.

11. The method as set forth in claim 9 wherein the liquid sterilant is a solution including said peracetic acid together with a buffer, and water.

12. The method of claim 11 wherein said solution further includes a detergent.

13. The method of claim 12 wherein said solution further includes corrosion inhibitors.

14. A microbial contamination removing apparatus comprising:
   a source of liquid rinse fluid;
   a means operatively connected with the source for removing a microbial contamination from the liquid rinse fluid;
   a module including a closure means which has opened and closed configurations therefore, where in the opened configuration, said module is opened to receive an item to be decontaminated, and in the closed configuration, said module isolates the received item from the ambient atmosphere and other sources of microbial contamination;
   a detachable module interconnecting means;

interconnecting tubing detachably connecting the source and said module means;

a means for selectively filling both the interconnecting tubing and the connected module with a liquid anti-microbial solution; and, a means for selectively keeping the interconnecting tubing and the module filled with the liquid anti-microbial solution for a sufficient duration to decontaminate the module, the item, the module interconnecting means, and the interconnecting tubing from the source to the module.

15. A method of removing microbial contamination from medical instruments, the method comprising:

disposing a medical instrument to be freed from microbial contamination in a storage module;

closing the module to penetration by microbial contaminates;

removably attaching the storage module with tubing which interconnects the attached module with a source of liquid rinse solution;

completely filling the interconnecting tubing from the module to the rinse solution source and the module with a liquid anti-microbial agent;

retaining the liquid anti-microbial agent in the module and the interconnecting tubing for a preselected duration, which preselected duration is sufficiently long to eliminate microbial contamination in the module, the medical instrument, and the interconnecting tubing;

passing a microbial contaminant-free liquid rinse solution from the rinse solution source only through the microbial contamination-free interconnecting tubing into the microbial contamination-free module to rinse the liquid anti-microbial agent from the interconnecting tubing, the module, and the medical instrument, whereby the liquid rinse solution passes only in contact with microbial contamination-free surfaces to prevent contamination of the liquid rinse solution.

16. A method of removing microbial contamination from items, the method comprising:

(a) enclosing an item to be freed of microbial contamination in an interior of a module which is closed to penetration of microbial contaminants from the ambient atmosphere;

(b) removably attaching the module with tubing that connects the module with a source of microbial contaminant-free rinse liquid;

(c) causing a liquid anti-microbial solution to flow into and remain in contact with the module interior and the tubing which connects the module with the source of rinse liquid until the item and the module interior are free of microbial contamination;

(d) draining the liquid anti-microbial solution from the module interior;

(e) passing a microbial contamination-free rinse liquid from the source thereof into the module interior to rinse the item;

(f) detaching the module while maintaining the module closed to microbial contaminants;

(g) storing the item in the module to retain its microbial contaminant-free condition.

17. A method of making an item free of microbial contamination, the method comprising:

enclosing the item in a chamber which is isolated from microbial contamination from the ambient atmosphere;

providing interior surfaces which define a liquid rinse flow path between the chamber and a source of microbial contamination-free rinse liquid;

causing an anti-microbial agent solution to flow into the chamber and into all flow path interior surfaces which define the interconnecting flow path from the liquid rinse source into the chamber and every interior surface in direct fluid communication therewith;

retaining the anti-microbial solution in the chamber and the interior surfaces until the interior surfaces, the item, and the chamber are free of microbial contamination, whereby freeing all surfaces between the rinse fluid source and the chamber of microbial contamination assures that the liquid rinse fluid will not carry microbial contaminants from contaminated surfaces into the chamber;

draining the antimicrobial solution from the chamber and the interconnecting flow path;

passing the liquid rinse fluid from the liquid rinse source only in contact with the microbial contamination free flow path surfaces into the chamber to rinse the item;

draining the liquid rinse fluid from the chamber and the interconnecting flow path.

* * * * *